US009239289B1

(12) United States Patent
Goldan

(10) Patent No.: US 9,239,289 B1
(45) Date of Patent: Jan. 19, 2016

(54) SPATIALLY RESOLVED DIFFUSIVE REFLECTANCE SPECTROSCOPY APPARATUS AND METHOD FOR USE THEREOF

(71) Applicant: MedView Technologies, Inc., Ontario (CA)

(72) Inventor: Amirhossein Goldan, Patchogue, NY (US)

(73) Assignee: MedView Technologies, Inc. (CA)

( * ) Notice: Subject to any disclaimer, the term of this patent is extended or adjusted under 35 U.S.C. 154(b) by 0 days.

(21) Appl. No.: 14/609,047

(22) Filed: Jan. 29, 2015

Related U.S. Application Data

(60) Provisional application No. 61/933,051, filed on Jan. 29, 2014.

(51) Int. Cl.
*G01J 5/02* (2006.01)
*G01N 21/49* (2006.01)
*G01B 11/22* (2006.01)

(52) U.S. Cl.
CPC ............ *G01N 21/49* (2013.01); *G01B 11/22* (2013.01); *G01N 2201/08* (2013.01)

(58) Field of Classification Search
CPC ........................ G02B 5/02; G01N 2021/174
See application file for complete search history.

(56) References Cited

U.S. PATENT DOCUMENTS

| 6,754,518 | B1 * | 6/2004 | Lloyd | A61B 5/0073 356/432 |
| 2003/0220549 | A1 * | 11/2003 | Liu | A61B 5/0059 600/317 |
| 2007/0232932 | A1 * | 10/2007 | Palmer | A61B 5/0071 600/476 |

OTHER PUBLICATIONS

Trong et al., "Spatially resolved diffuse reflectance in visible and near-infrared wavelength range for non-destructive quality assessment of 'Braeburn' apples," 2014, Postharvest Biology and Technology, vol. 91, pp. 39-48.*

* cited by examiner

*Primary Examiner* — Kiho Kim
(74) *Attorney, Agent, or Firm* — The Farrell Law Firm, P.C.

(57) ABSTRACT

Provided is a spatially resolved diffusive reflectance spectroscopy apparatus that includes an emitter, a plurality of optical waveguides, a switch, a photon detector, and a controller, and a method for operation of the apparatus. The controller controls emitter intensity, identifies photons detected by the photon detector as belonging to a specific optical waveguide of the plurality of optical waveguides, counts the detected photons, and identifies respective optical waveguides receiving each counted photon. The emitter emits optical photons in an optically turbid medium, and a distal end of each optical waveguide of the plurality of optical waveguides receives the optical photons reflected or scattered in the optically turbid medium.

20 Claims, 2 Drawing Sheets

210 — Receive Optical Photons Reflected/Scattered in Optically Turbid Medium

220 — Count Detected Photons

230 — Identify Specific Optical Waveguide Having Received Specific Photons

240 — Identify Depth Within Medium

Fig. 2

SPATIALLY RESOLVED DIFFUSIVE REFLECTANCE SPECTROSCOPY APPARATUS AND METHOD FOR USE THEREOF

PRIORITY

This application claims priority to U.S. Provisional Application No. 61/933,051, filed Jan. 29, 2014, the entire content of which is incorporated herein by reference.

BACKGROUND OF THE INVENTION

1. Field of the Invention

The present invention relates generally to the field of optical imaging. More particularly, the invention concerns an apparatus for combining fluorescence, reflectance and diffuse reflectance spectroscopy for vein locating and sample imaging, and a method of operation thereof.

2. Description of the Related Art

Transport of light that undergoes Brownian random walk at a microscopic level is described macroscopically using diffusion theory. Tracking of individual light photons at each scattering event has proven to be very complicated.

Conventional systems fail to provide an accessible solution that offers high-sensitivity, non-destructive, non-invasive, portable and cost effective analysis to detect features within turbid media. Conventional systems do not provide a non-invasive method to locate veins and corresponding depths of veins beneath the skin of living biological tissue, to perform vein location for venipuncture.

Provided herein is an apparatus and method that provides three-dimensional remote optical sensing of objects within turbid media to identify depth and location within the turbid media, for example to identify one or more veins with corresponding depths within biological tissue via tracing of photons and average motion of a cloud of light photons after scattering events.

SUMMARY OF THE INVENTION

The present invention overcomes the above shortcomings by providing a spatially resolved diffusive reflectance spectroscopy apparatus that includes an emitter, a plurality of optical waveguides, a switch, a photon detector, and a controller. The controller controls emitter intensity, identifies optical photons detected by the photon detector as belonging to a specific optical waveguide of the plurality of optical waveguides, counts the detected photons, and identifies respective optical waveguides receiving each counted photon. The emitter emits near infrared light in an optically turbid medium, and a distal end of each optical waveguide of the plurality of optical waveguides receives the near infrared light reflected or scattered in the optically turbid medium.

BRIEF DESCRIPTION OF THE DRAWINGS

The above and other objects, features and advantages of certain exemplary embodiments of the present invention will be more apparent from the following detailed description taken in conjunction with the accompanying drawings, in which:

FIG. 2 is flowchart of a method of a preferred embodiment of the present invention.

DETAILED DESCRIPTION OF THE PREFERRED EMBODIMENTS

Figure 1:
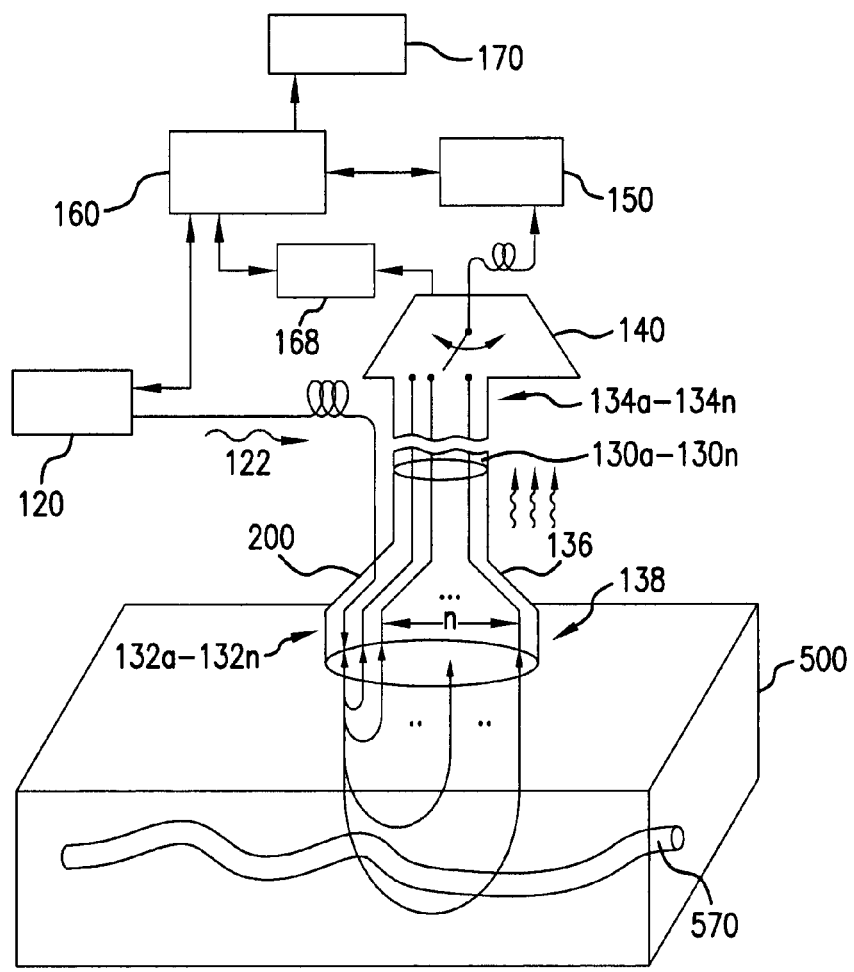
FIG. 1 is block diagram of an apparatus of a preferred embodiment of the present invention.

The following detailed description of preferred embodiments of the invention will be made in reference to the accompanying drawings. In describing the invention, explanation of related functions or constructions known in the art are omitted for the sake of clarity in understanding the concept of the invention that would otherwise obscure the invention with unnecessary detail.

For backscattering spectroscopy, a technique is provided to detect an object within turbid media via spatially resolved diffusive reflectance measurements. As described herein, depth of the object is identified by a photon path distribution function from one source to a detector. Considering a source-to-detector separation and a homogenous turbid medium, photon path distribution has a banana shape extending from the source emitter to detector. In a medium with weak absorption, a modal line shaped as a photon banana, i.e., a curve running along the center of the banana with a highest probability of photon migration, is related to a source to detector separation, $r_{sd}$, reaching a maximum depth, $z_{max}$, according to Equation (1):

$$z_{max} \propto r_{sd} \quad (1)$$

As described herein and shown in FIG. 1, a single source emitter (120) provides photons (122) receivable by a series of distal ends (132a-132n) provided at predetermined distances from each other. In a preferred embodiment of the present invention, a spatially resolved diffusive reflectance spectroscopy apparatus (100) is provided that includes emitter (120) that emits optical photons (122) in optically turbid medium (500), and a plurality of optical waveguides (130a-130n) that receive the optical photons (122) after being reflected or scattered in the optically turbid medium.

Apparatus (100) includes a switch (140), a photon detector (150) and a controller (160), which preferably includes an analog processing unit that processes an analog signal of detector (150), provides filtering to de-noise the signal, amplifies the signal to increase a signal-to-noise ratio (SNR), and pulse shapes the analog signal for digitization.

Controller (160) preferably includes a digitizer that discriminates, compares and converts an analog signal to a digital signal. Apparatus (100) preferably includes a probe that mechanically imprints a spot identifying a location of an optimal vein (510). Probe (200) is spatially separated from each distal end of each optical waveguide of the plurality of optical waveguides connected to switch (140), with the spatially separation covering a range of emitter to detector separation distances. Apparatus (100) preferably includes a display (170) that displays a location of vein (510) for venipuncture.

Controller (162) preferably controls intensity output of emitter (120), with a relatively lower emitter intensity used for detector waveguides with small source-to-detector distances and a relatively higher emitter intensity used for detector waveguides with large source-to-detector distances. Controller (160) operates emitter (120) continuously on during exposure or pulse mode modulates emitter (120) at a predefined frequency during exposure. For spectroscopy, controller (160) tunes a peak wavelength for each exposure and scans a range of wavelengths.

Emitter (120) emits optical photons (122) via emitter optical waveguide (136) that is separate from and positioned apart from the plurality of optical waveguides (130a-130n). Emitter optical waveguide (136) has a distal end configured to project the optical photons (122) on turbid medium (150), for detection of a depth of vein (510) or other object of interest within turbid medium (150). In a preferred embodiment, emitter (120) is a point light source that penetrates into the optically turbid medium (510) and emits the optical photons (122) preferably as near infrared light in wavelengths ranging from 400 to 1,200 nanometers, via continuous or picosecond pulsed waves.

Counter (168) preferably counts only analog shaped signals above a threshold voltage to exclude noise. Counter (168) counts digitized signals during a specified exposure time, i.e., observation time. For each individual exposure, the exposure time is the time during which emitter (120) is turned on and emits photons at a defined wavelength and a detected analog signal is processed, digitized and counted, with an increasing digitized, i.e., counted, value. Exposure time determines the duration during which all detected signals contribute to a single digitized value, and each photon detected within the exposure time increments a same counter. At the end of one exposure, the counted value is stored and the counter is reset for a next exposure.

Controller (160) preferably includes a digital processing unit that synchronizes light emission to fiber switching, light detection, signal digitization, and counting, to identify the detected photons belonging to a detector waveguide in a fiber bundle, i.e., in one waveguide of the plurality of optical waveguides (130a-130n).

Switch (140) sequentially connects each proximal end (134a-134n) of each optical waveguide of the plurality of optical waveguides to detector (150), under control of controller (160).

Controller (160) selects a required exposure time during which photons are being counted. Certain optically turbid medium (500) is highly absorbing, with few photons being reflected, with a low reflectance photon flux, for which longer exposure times are utilized to collect and detect a signal having a high SNR. Controller (160) controls storing of digitized signal data for counting by counter (168), identifying specific distal ends (132a-132n) of each optical waveguide of the plurality of optical waveguides. Controller (160) identifies photons as having been emitted by emitter (120), making detected random photons, i.e., photons not emitted by emitter (120), irrelevant.

Photons emitted by emitter (120) that travel back from within the turbid media are back-scattered and picked up at distal ends (132a-132n) of respective optical waveguide of the plurality of optical waveguides. The photons are detected and identified by respective optical waveguides receiving each counted photon for depth detection.

Distal ends (132a-132n) of each optical waveguide of the plurality of optical waveguides (130a-130n) are spatially separated by one or more predefined distances from each other distal end of the other optical waveguides of the plurality of optical waveguides (130a-130n). Based on the identified specific optical waveguide that receives each counted photon, controller (160) identifies a depth and three dimensional position of an object within the optically turbid medium, up to a depth penetration of twenty to twenty-five millimeters in a human skin layer, and up to ten centimeters in other turbid media.

Apparatus (100) provides a single photon count from visible to infrared range of the light spectrum, with real-time spatially-resolved spectroscopy (SRS) over a spatial range of up to one hundred millimeters, while switching among up to one hundred fibers, to facilitate real time analysis of objects within turbid media, up to three centimeters in depth, by scanning the surface of the media. The apparatus is capable of detecting the signal over large source to detector distances, up to one hundred millimeters.

As shown in FIG. 2, in a preferred embodiment of the present invention, a method is provided for detecting depth of an object within optically turbid medium (150). In step 210, reflected optical photons are received, via a plurality of optical waveguides, after being reflected or scattered in the optically turbid medium. Photon detector (150) identifies photons belonging to a specific optical waveguide of the plurality of optical waveguides, and the detected photons are counted in step 220. Respective optical waveguides receiving the counted photons are identified in step 230, and depth of the object within the optically turbid medium is determined based on the identified respective optical waveguides receiving the counted photons in step 240.

Accordingly, provided are an apparatus and method that exploit propagation and distribution of light in an optically turbid medium, e.g., human tissues. A point light source of either continuous wave or picosecond pulsed wave penetrates into a scattering and absorbing medium, with exit position of radial decaying dependence of the photons, which are diffusely reflected, from the medium defining optical properties of the optically turbid medium. The diffuse reflectance from the optically turbid medium is collected spatially using a contact probe that includes of a series of waveguides at predetermined spacing.

Accordingly, provided is a non-invasive platform for study of materials, gas, liquids, and solids for industry and scientific applications that include biological tissue imaging for medical diagnostics, three dimensional vein detection, epidural injection positioning, cancer detection, in-vivo skin lesion imaging, non-invasive blood analysis, food inspection, material microstructure analysis, real-time assembly line defect detection, chemical composition analysis, real-time pharmaceutical manufacturing quality control, and multilayer turbidity measurement.

While the invention has been shown and described with reference to certain exemplary embodiments of the present invention thereof, it will be understood by those skilled in the art that various changes in form and details may be made therein without departing from the spirit and scope of the present invention as defined by the appended claims and equivalents thereof.

What is claimed is:

1. A spatially resolved diffusive reflectance spectroscopy apparatus comprising:
   an emitter configured to emit optical photons into an optically turbid medium;
   a plurality of optical waveguides, with each optical waveguide of the plurality of optical waveguides including a distal end configured to receive the optical photons reflected or scattered in the optically turbid medium;
   a photon detector; and
   a controller configured to obtain a count of a plurality of photons detected by the photon detector and identify a specific optical waveguide of the plurality of optical waveguides that receives each photon of the plurality of counted photons.

2. The apparatus of claim 1, wherein each distal end of each optical waveguide of the plurality of optical waveguides is spatially separated along a surface of the optically turbid medium by a predefined distance from other distal ends of other optical waveguides of the plurality of optical waveguides.

3. The apparatus of claim 1, further comprising a switch configured to sequentially connect each proximal end of each optical waveguide of the plurality of optical waveguides to the photon detector.

4. The apparatus of claim 1, further comprising an emitter optical waveguide having a distal end configured to project the optical photons into the turbid medium,
wherein a distal end of the emitter optical waveguide is spatially separated from each distal end of each optical waveguide of the plurality of optical waveguides by a predetermined distance.

5. The apparatus of claim 4, wherein the distal end of the emitter is configured as a point light source that penetrates into the optically turbid medium.

6. The apparatus of claim 1, wherein the controller is further configured to identify a depth of an object within the optically turbid medium, based on identification of the specific optical waveguides that receive each of the plurality of counted photons.

7. The apparatus of claim 1, wherein the optical photons are emitted as near infrared light for locating a vein in the optically turbid medium.

8. The apparatus of claim 7, further comprising a display configured to display a location of the vein.

9. The apparatus of claim 7, further comprising a probe configured to mark a location identifier of the vein.

10. A method for detecting depth within optically turbid medium, the method comprising:
receiving, via a plurality of optical waveguides, optical photons reflected or scattered in the optically turbid medium;
counting the received photons; and
identifying specific optical waveguides of the plurality of optical waveguides that receive respective specific counted photons,
wherein depth within the optically turbid medium is determined based on the specific optical waveguides identified as receiving respective counted photons.

11. The method of claim 10, wherein a distal end of each optical waveguide of the plurality of optical waveguides is configured to receive the optical photons after being reflected or scattered in the optically turbid medium.

12. The method of claim 11, further comprising projecting the optical photons into the turbid medium at a location on a surface of the turbid medium at a distance spatially separated from each distal end of each optical waveguide of the plurality of optical waveguides.

13. The method of claim 11, wherein each distal end of each optical waveguide of the plurality of optical waveguides is spatially separated by a predefined distance along a surface of the optically turbid medium from each other distal end of other optical waveguides of the plurality of optical waveguides.

14. The method of claim 13, wherein proximal ends of each optical waveguide of the plurality of optical waveguides are sequentially connected to a first end of a switch.

15. The method of claim 14, further comprising switching each of the proximal ends of each optical waveguide to a photon detector connected to a second end of the switch.

16. The method of claim 10, wherein the optical photons are near infrared light photon emitted to locate a vein in the optically turbid medium.

17. The method of claim 16, further comprising displaying, on a display, a location of the vein, based on the determined depth.

18. The method of claim 10, wherein the optically turbid medium is one of a liquid and a gas.

19. The method of claim 10, wherein the determined depth in the optically turbid medium identifies a crack in a pharmaceutical tablet.

20. The method of claim 19, wherein the crack in the pharmaceutical tablet detected in real time during assembly line manufacture of the pharmaceutical tablet.

* * * * *